(12) United States Patent
Wong et al.

(10) Patent No.: US 7,004,961 B2
(45) Date of Patent: Feb. 28, 2006

(54) MEDICAL DEVICE AND METHOD FOR TEMPERATURE CONTROL AND TREATMENT OF THE BRAIN AND SPINAL CORD

(76) Inventors: Edward Wong, 23 St. Tropez, Newport Beach, CA (US) 92660; Edward R. Zaleski, 1272 Brittany Cross Rd., Santa Ana, CA (US) 92705; Anshul Varshney, 2291 Wandering Ridge Dr., Chino Hills, CA (US) 91702

( * ) Notice: Subject to any disclaimer, the term of this patent is extended or adjusted under 35 U.S.C. 154(b) by 53 days.

(21) Appl. No.: 10/741,484

(22) Filed: Dec. 19, 2003

(65) Prior Publication Data

US 2004/0138728 A1    Jul. 15, 2004

Related U.S. Application Data

(60) Provisional application No. 60/438,904, filed on Jan. 9, 2003.

(51) Int. Cl.
*A61F 7/00* (2006.01)
(52) U.S. Cl. .................................. 607/105; 607/104
(58) Field of Classification Search .............. 607/97, 607/104–107, 113; 604/113–114
See application file for complete search history.

(56) References Cited

U.S. PATENT DOCUMENTS

| | | | |
|---|---|---|---|
| 6,083,148 A * | 7/2000 | Williams | 600/2 |
| 6,217,552 B1 * | 4/2001 | Barbut et al. | 604/113 |
| 6,572,640 B1 * | 6/2003 | Balding et al. | 607/105 |
| 6,699,269 B1 | 3/2004 | Khanna | |
| 6,849,072 B1 * | 2/2005 | Lee et al. | 606/21 |
| 6,899,726 B1 * | 5/2005 | Larnard et al. | 607/105 |
| 2002/0120317 A1 | 8/2002 | Fletcher | |
| 2002/0198579 A1 | 12/2002 | Khanna | |
| 2003/0055473 A1 | 3/2003 | Ramsden et al. | |
| 2003/0130651 A1 | 7/2003 | Lennox | |
| 2003/0163181 A1 | 8/2003 | Frazer et al. | |

* cited by examiner

*Primary Examiner*—Roy D. Gibson
(74) *Attorney, Agent, or Firm*—Walter A. Hackler

(57) ABSTRACT

The invention provides a medical device having a thermister for temperature measurement, irrigation/aspiration ports for fluid exchange and application of therapeutic modalities, a pressure manometer for pressure measurement, and an external system for control of temperature, pressure, and flow rate. When applied to the central nervous system (CNS), this device can be used in hypothermia or hyperthermia applications, the exchange of cerebral spinal fluid (CSF), the application of treatment modalities, and the insertion of a ventriculostomy or ventriculostomy-like unit. When applied to spinal cord applications, this device can provide temperature control and a method for application of treatment modalities by using a venting device placed in the space surrounding the spinal cord, a device with similar instrumentation to measure temperature and pressure. A device for ultrasound localization of the CNS device is described. A device for a fiber optic endoscope for visualization and localization is also described. Method of using the devices in treating patients suffering from cardiac arrest, circulatory arrest, exsanguination, head or neck trauma, strokes, tumors and other intracranial diseases are disclosed. In the case of hypothermia treatment of the brain, rapid cooling using principles of convection and conduction will be applied to the lateral ventricle and subarachnoid and/or subdural space simultaneously where the neurons are located in close proximity.

23 Claims, 12 Drawing Sheets

MEDICAL DEVICE AND METHOD FOR TEMPERATURE CONTROL AND TREATMENT OF THE BRAIN AND SPINAL CORD

This application relies on the priority date of Provisional Patent Application Ser. No. 60/438,904 filed Jan. 9, 2003.

FIELD OF THE INVENTION

The present invention generally relates to medical devices useful in 1) extending the critical period of brain death to allow for resuscitation in cardiac arrest, exsanguination, and other causes of circulatory arrest; and 2) reducing and preventing brain injury or spinal cord injury in patients with head or neck trauma, strokes, tumors, and other intracranial diseases. More specifically, the invention provides devices for insertion into the lateral ventricle(s) of the brain and the space (including the subarachnoid/subdural space) surrounding the brain and the spinal cord for use in hypothermia or hyperthermia applications, the exchange of cerebrospinal fluid (CSF), the application of treatment modalities, and the insertion of a ventriculostomy unit.

BACKGROUND OF THE INVENTION

Brain death usually occurs within five to 10 minutes of cessation of blood to the brain seen in cardiac arrest, circulatory arrest, shock, exsanguination, cerebrovascular accidents (CVA's or strokes), or other cause of ischemia or anoxia to the brain. An approach to forestall the results of ischemia or anoxia to the brain will allow the treating physician to have more time to save the life of the patient. Specifically, if an approach to sparing the neurons (cell bodies of the functional brain or grey matter) of the central nervous system (CNS) immediately and over a rapid time interval, the white matter (axons), then the physician can more readily save the patient with circulatory arrest or other causes of brain ischemia. In effect, it is desirable to have a state of suspended animation in which the brain will have little damage due to ischemia or anoxia.

Trauma to the brain and/or spinal cord may result in direct injury to the central nervous system (CNS) tissue as well as to swelling or edema of this tissue against the walls of the skull or spinal canal. In the case of hemorrhage, there may be compression of the brain or spinal cord from within or around the tissue. After a period of time (minutes to hours to days), death of the tissue may occur causing irreversible damage.

Pathology to the brain may occur due to blunt injuries, such as a blow to the head, resulting in hemorrhage within or around the brain and associated swelling of brain tissue. Stroke, tumor, or other intracranial disease may also cause hemorrhage or swelling of brain tissue. Diagnosis of these diseases is made after careful neurological examination that is confirmed by imaging procedures including M.R.I., C.T., and ultrasound studies of the brain. Unfortunately, it is often difficult to control injury to the brain using conventional neurosurgical means including medical and surgical intervention.

Spinal injury may occur in blunt trauma due to a direct blow or to coup-countercoup injury. There may be direct pressure placed on the spinal cord as a result of a fractured or dislocated vertebral body (-ies) or disc, resulting in sensory and motor deficits below the level of the lesion. The mechanism of spinal injury is often related to swelling of the tissues of the spinal cord. Immediate treatment must be administered to prevent or diminish the effects of spinal cord compression and tissue edema.

Spinal cord ischemia may also occur during or following surgery on the aorta, including abdominal aneurysm repair with a prosthetic graft. Motor, sensory, and autonomic functions may be severely compromised or lost if the spinal cord is made ischemic. In the case where brain cooling can result in an extended period of resuscitation, spinal cord ischemia may occur. Therefore, hypothermia of the brain in resuscitation should be accompanied with hypothermia of the spinal cord.

Current treatment for swelling of the brain or spinal cord is not always satisfactory. In the severely injured brain or spinal cord, medical therapy to control swelling is usually applied systemically resulting in high levels of medication in the rest of the body with very low concentrations reaching the brain or spinal cord. Surgical intervention to decompress the brain or spinal cord requires major intervention through opening the skull or spinal column to expose the area and prevent compression against the fixed volume of the bony walls. Ventriculostomy (placing a tube into the lateral ventricle of the brain) is usually not performed acutely, and by the time it is used in the sub-acute phase, there may already be permanent damage to the brain.

Hypothermia has proved encouraging in the recent literature for the purpose of decreasing oxygen consumption and for decreasing swelling of CNS tissue. Unfortunately, cooling of the entire body to cool the brain or spinal cord does have inherent dangers. The heart responds to hypothermia with arrhythmias, and the blood clotting mechanisms may be severely impaired resulting in hemorrhage. Moreover, cooling the body only results in a few degrees of cooling of the CNS. This may be due to protective mechanisms in the hypothalamus of the brain, or due to difficulty in heat/cold exchange between the blood and the brain.

With the new technologies now available, it is time for a new approach to controlling the temperature of the CNS as well as administering medications to the CNS directly in a continuous fashion.

SUMMARY OF THE INVENTION

The present invention provides devices and methods for preventing or slowing brain death following processes of ischemia or anoxia to the brain including cardiac arrest, circulatory arrest, exsanguination, cerebrovascular accidents (CVA's or strokes), shock, and other causes. In order to preserve the brain from ischemia, it is necessary to rapidly cool the neurons (cell bodies of the functioning CNS) located in the cerebral cortex, paraventricular nuclei, and other centers. This may be achieved by cooling both compartments of the lateral ventricle and the subarachnoid space simultaneously. Convection cooling coupled with conduction cooling will rapidly cool the neurons, while the white matter (axons of the neurons) will cool by transmission of conduction cooling. This approach will rapidly cool the brain and prevent ischemic injury and edema of the brain tissue. In order to prevent ischemic damage to the spinal cord during extended resuscitation, it is necessary to transmit the cooling effect through the subarachnoid space surrounding the spinal cord. This can be accomplished with this device, but it may require a vent in the subarachnoid space (e.g. lumbar puncture or similar method).

The invention further provides devices and methods for preventing or minimizing brain and/or spinal cord injury following trauma, CNS edema, ischemia, stroke, inflammation, infection, etc. It may also be used for cooling the brain and/or spinal cord prior to and during surgical intervention. In addition, the brain and/or spinal cord may have other thermoregulation including warming/heating the tissue before, during, and after therapeutic intervention. Moreover, the principles of this invention may be applied to other organs in the body for thermoregulation, hypothermia, and application of circulating fluids with/without pharmaceutical agents.

Apparatus of the present invention is used to prevent neurological damage by selective central nervous system (brain and/or spinal cord) cooling. The apparatus includes a flexible, hollow conduit with a distal and proximal end. The distal end of this conduit penetrates the brain through a surgical opening in the skull to reside within the lateral ventricle and/or subarachnoid and/or subdural space of the brain, while the proximal end projects outside the skull. Prior to the insertion of the conduit, a stylet may be inserted through the proximal end up to the tip of the distal end of the conduit to increase it's tensile strength for ease of insertion into the brain/lateral ventricle/subarachnoid space, much like the modern day insertion of a ventriculostomy tube. A guide sleeve or conduit may be inserted to facilitate insertion and retraction of multiple instruments for treatment and for monitoring physiological and instrument parameters.

The stylet may include a fiber-optic camera and/or ultrasound navigational instrumentation If this fiber-optic camera is inserted into the conduit, the rigid lens at the distal end of the conduit allows the conduit to penetrate through the surgical opening in the skull as well as the brain parenchyma to any region of the brain including the subarachnoid and/or subdural space and/or the lateral ventricle, or any other opening in the central nervous system (CNS).

After the conduit is inserted into the lateral ventricle and/or subarachnoid and/or subdural space, the fiber optic camera may be manipulated within the brain parenchyma or subarachnoid space or lateral ventricle to visualize the adjacent area for proper placement of the flexible conduit. When the flexible conduit is verified to be properly aligned within the brain, the stylet/fiber optic camera is withdrawn from the proximal end and the conduit is secured to the skull and/or surrounding tissue.

Backflow of CSF should occur after the removal of the stylet which ensures that the conduit is inserted into the lateral ventricle and/or subarachnoid and/or subdural space and has a direct connection between the ventricular system and/or subarachnoid and/or subdural space of the brain and the outside milieu. A one-way valve or other suitable device may be placed at the proximal end of the flexible conduit to prevent the continual drainage of CSF from the brain. In cases of brain herniation/movement, the conduit bends in the direction of herniation/movement, thus eliminating/minimizing CNS injury.

With the hollow conduit securely in place, one embodiment of an elongate device may be used to induce hypothermia/hyperthermia selectively within the intraventricular and/or subarachnoid and/or subdural space of the CNS. The device is inserted through the proximal end of the flexible conduit and comprises cooling/heating, circulating, temperature and pressure monitoring components.

The embodiment may achieve the goal of cooling/heating the CSF within the brain by circulating hot or cold fluid inside a balloon which is disposed within a lateral ventricle of the brain or other spaces in the brain such as, for example, subarachnoid spaces. By the process of conduction, convection, and radiation, the circulating fluid flowing at a desired temperature within the balloon will induce a change in the surrounding CSF temperature to the desired level without any contact being made between the fluid in the balloon and the CSF.

The device may include a hollow device with a balloon attached at its distal end (balloon covering the outer lip of the probe's distal end). Two catheters are disposed parallel to one another within the probe, and are attached inside the lumen of the balloon at the distal end of the catheter.

Exiting the device at their proximal end, catheters A & B will be connected in series by hollow tubing. The hollow tubing will, in turn, be coupled to a pump, a temperature regulator, and a pressure regulator. Furthermore, four other catheters (C, D, E, and F) may be disposed parallel to the first two catheters A & B within the probe. The purpose of catheters C, D, E, and F is to circulate CSF within the brain. A separate needle septum connected to either catheter's C, D, E, and/or F may be used to administer pharmacological agents, fluids, and/or other compounds into the brain.

Catheters C & D may be connected to each other in series at their proximal ends as can catheters E & F with hollow tubing (hollow tubing different from that connected to catheters A & B) after exiting the device at the proximal end. Separate pump(s) may also be attached to the hollow tubing which connects catheters C & D serially and catheters E & F serially. The distal end of catheters C & D may be in direct contact with the CSF in the lateral ventricle, thus they exit the probe's distal end around the balloon or through side ports in the probe, also located at the distal end. Catheters C & D may also be connected to a control system. The distal ends of catheters E & F may be in direct contact with the CSF in the subarachnoid/subdural space(s) through side ports of the cooling and/or heating and/or circulating medical device.

When emerging around the balloon, the distal ends of catheters C, D, E, & F curve outward (up to 180° of each other) in the lateral ventricle and subarachnoid/subdural space(s), respectively to ensure optimal circulation of CSF and to protect against occlusion of the catheter tip.

Alternatively, CSF circulation may be achieved by placing the tip of one catheter in the lateral ventricle while the other catheter resides in the subarachnoid space (FIG. 10). In this case, the distal end of catheter C will reside in the lateral ventricle through openings in the probe's distal end around the balloon or in a side port, while the distal end of catheter D may exit a side port near the subarachnoid space in the probe. Circulation is achieved by the pump which aspirates fluid in catheter C that is redeposited through catheter D. The flow may be reversed in C & D.

In addition to the heating/cooling and circulating mechanisms, this device is able to monitor CNS temperature and pressure within the ventricular and subarachnoid space as well as the brain parenchyma.

The device may have pre-drilled bores, or tunnels, within the walls which run parallel to the axis of the lumen (long axis). These tunnels may be used to insert a thin pressure transducer, the distal tip of which will reside in the lateral ventricle. Furthermore, the tunnels within the walls of the device may also have side holes drilled into the wall. This will allow thermisters to obtain temperatures at different levels of the brain. This device with the aforementioned attachments and modifications may be inserted at its distal end into the proximal end of the secured conduit all the way down the conduit and into the lateral ventricle with the balloon deflated.

The proximal end of the device may be exposed to the outside milieu while the distal end with the balloon attachment may be submerged in the lateral ventricle making direct contact with the CSF. This device is made of flexible material, thus is able to bend to prevent/minimize brain injury in case of brain movement. Once the device is secured, heating/cooling of the brain can be achieved by using the pump connected to catheters A & B to irrigate catheter A, while catheter B aspirates the same fluid, thus creating a cycle of flow within the balloon. The temperature of the fluid in the balloon is monitored through a thermister in catheter A while the CSF and brain temperatures are monitored through the thermisters in the probe. The pressure within the CSF is also monitored with a pressure transducer in the tunnels of the probe. Adjustments of the pressure and temperature can be made manually or automatically through the pressure transducer and temperature regulator. CSF flow is achieved with activation of the pumps connected to catheters C & D as well as E & F. Catheter D & F aspirates the CSF while catheter C & E irrigates the CSF, thus creating CSF flow within the lateral ventricle and/or subarachnoid space simultaneously.

In addition to the circulation scheme depicted above, several variations, or embodiments, of the present invention may be utilized to aid in selective cooling of the CNS. Unless otherwise specified, the following embodiment describes the same catheters C & D attached at their proximal end by a hollow tube which is connected to a pump.

One embodiment involves placing the distal end of catheter C within the lateral ventricle through the flexible conduit. However, in this case, catheter D is inserted through a surgical opening in the skull, at its distal end, to the subarachnoid space of the brain instead of the lateral ventricle. Catheter D may be inserted within the same flexible conduit, at a new location near the conduit through a different surgical opening to the subarachnoid space, or anywhere through a new surgical opening in the entire skull to the subarachnoid space.

It should be noted that catheter C and D may be interchanged, where catheter D's distal end lies in the lateral ventricle through the flexible conduit, while catheter C is inserted into the subarachnoid space through a new surgical opening in the skull or through the flexible conduit.

Another embodiment, again involves placing the distal ends of either catheter C or D through the flexible conduit into the lateral ventricle of the brain. However, in this case the complementary catheter (C or D) is inserted into the subarachnoid space of the spinal cord anywhere from the cervical region to the end of the spinal cord in the lumbosacral region. This is achieved by either doing a lumbar puncture or under fluoroscopic guidance a spinal tap with catheter insertion through the lumbar, thoracic, cervical spinal segments, or cisternal tap. The flow of CSF will be either from a raustral-caudal direction or a caudal-raustral direction.

Yet another embodiment involves a slightly different setup compared to the previous ones described. In this scenario, the same device is inserted into the flexible conduit and circulation of CSF occurs in the intraventricular area as described in the original description. However, a separate spinal tap needle is used to aspirate spinal fluid from the lumbar region of the patient. The aspiration of the spinal fluid allows CSF fluid within the brain to flow down to the spinal cord, thus allowing spinal cooling. In order to replenish CSF which has been lost to spinal aspiration, a pressure regulator compensates for any loss of pressure by drainage of spinal fluid through the tap with artificial spinal fluid, lactated ringer, or any pharmacological agent to be administered into the ventricular/subarachnoid space.

To facilitate CSF flow, the patient may lie in or be moved to a supine, prone, lateral decubitus (left or right side), trandelinburg, reverse-trandelinburg, vertical with head up, vertical with head down, or any other position with the patient's own power or through the use of an electronic stretcher/table/chair to circulate CSF in the direction of the spine, brain, or area of desired circulation.

A further embodiment of the medical device used for selective cooling/heating of the central nervous system involves the use of a similar device as hereinabove described. However, in this case there is no balloon at the distal end of the probe. This device uses the same 4 or 6 catheters identified in derivative 1 (A, B, C, D, E, and/or F) which lie parallel to one another in the lumen of the probe. Catheters A & B are in serial connection with one another at their proximal ends through the use of hollow tubing. The hollow tubing is connected to a pump, temperature and pressure regulator.

The distal tips of catheter A & B curve outward (up to 180° of one another) out of the distal end of the device or through side ports located in the distal end of the probe. The curve out of the distal end of the device will ensure that CSF will flow optimally and will minimize obstruction of the catheter tips. Catheter C & D's distal tip will also emerge from the distal end of the probe.

This embodiment enables various instruments to be inserted into the conduit or individual catheters. Either catheter may be used to insert an ultrasound device into the proximal end all the way out of the distal end. Moreover, a fiber-optic tube may also be interchanged with the ultrasound device to visualize intra-cerebral spaces along the length of the device and within the ventricles. Alternatively, an electrocautery device may be inserted through either catheter C, D, E, and/or F which allows a neurosurgeon to cauterize a bleeding vessel visible through the ventricular system. Furthermore, catheters C, D, E, and/or F can be used more conventionally to insert a thermister or pressure transducer.

A thermister and pressure transducer may be located in the bore present in the walls of the device whether or not they will be used in catheters C, D, E, and/or F. The distal end of this device with the aforementioned attachments may be inserted into the secured conduit's proximal end and advanced all the way down into the lateral ventricle of the brain. The device will then be secured. The pump attached to the proximal ends of catheter A & B will aspirate fluid from catheter A and irrigate the same CSF into catheter B.

While this fluid circulates in this loop, the temperature regulator attached to the hollow tubing will cool or heat the cerebrospinal fluid to the desired temperature. The tip of the thermister located within the lateral ventricle will monitor the intraparenchymal and/or intraventricular and/or subarachnoid temperature.

Adjustments of the temperature regulator can be made manually or be set to a desired temperature with the temperature regulator automatically cooling or heating the CSF to achieve the set goal. The pressure transducer will monitor the pressure within the intracerebral area. An increase in pressure beyond a set point will increase the aspiration of fluid through catheter A.

Conversely, a decrease in pressure below a set point will increase irrigation through catheter B.

The invention relates to a medical device useful in reducing and preventing brain death, brain injury or spinal cord injury in patients with head or neck trauma, strokes, tumors, and other intracranial diseases. The prevention of brain death as a result of cardiac arrest, exsanguination, circulatory arrest, shock, etc. will give the treating physician more time to successfully resuscitate the patient.

More specifically, the invention provides devices for insertion into the lateral ventricle(s) and subarachnoid space of the brain and the space (including the subarachnoid space) surrounding the spinal cord for use in hypothermia or hyperthermia applications, the exchange of cerebral spinal fluid (CSF), the application of treatment modalities, and the insertion of a ventriculostomy unit.

The medical device has within its length two or more thermisters for temperature measurement, a fiber optic endoscope and/or ultrasound navigational device for visualization and localization, irrigation/aspiration ports for fluid exchange and application of therapeutic modalities, and a pressure manometer for pressure measurement. An external system housed in a compact unit the size of a brief case controls temperature, pressure and flow rate. Ultrasonic localization of the lateral ventricle may be coupled with the fiber-optic endoscope ensuring rapid and accurate insertion of the instrument into the CSF of the lateral ventricle. The design of the instrument allows rapid transfer of learning skills for any neurological surgeon, emergency physician, or other trained medical personnel to perform the ventriculostomy (or surgical opening in the head) with a minimum of training and with unparalleled accuracy within minutes.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
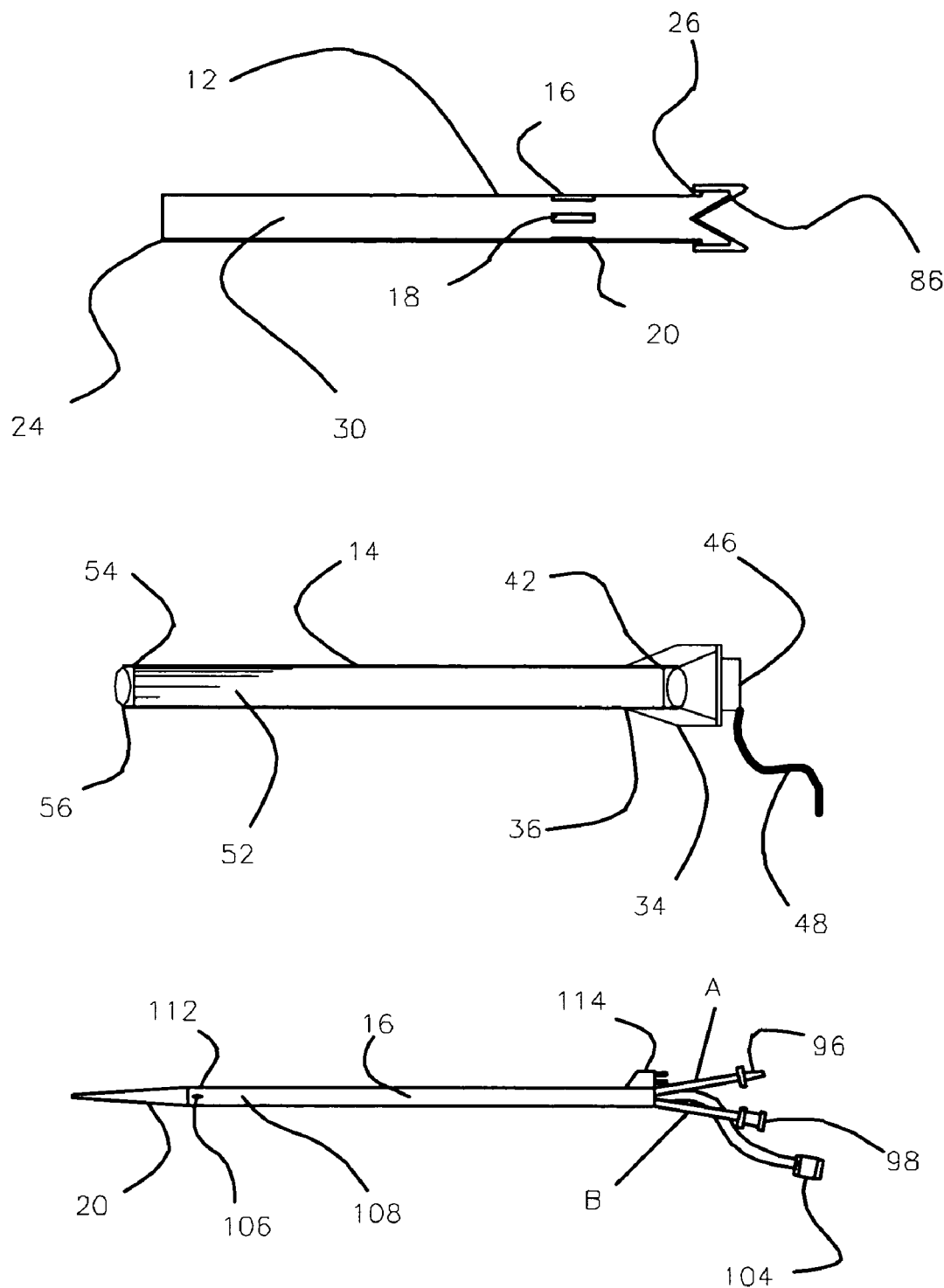
FIG. 1 shows apparatus in accordance with the present invention generally including an elongated conduit, a stylet for insertion into the conduit, as hereinafter described, and an elongated cooling device also insertable into the conduit as hereinafter described.

With reference to FIG. 1, there is shown apparatus 30 in accordance with the present invention generally including a conduit 12, a stylet 14 and an elongated cooling device, or probe, 16 having a balloon 20, shown deflated in FIG. 1.

The conduit 12 is flexible and hollow with a distal end 24, a proximal end 26 and a lumen 30 for insertion of the stylet 14 and device 16, as hereinafter described, side ports 16, 18, 20 may be provided in the conduit 12.

The stylet 14 includes a light source 34 disposed at a proximal end 36 of the stylet 14 along with a focusing element 42. Power to the light source 34 is provided through lines 46, 48.

The stylet 14 includes fiber optics 52 communicating with a lens/camera 54 disposed at a distal end 56 of the stylet 14.

Figure 2:
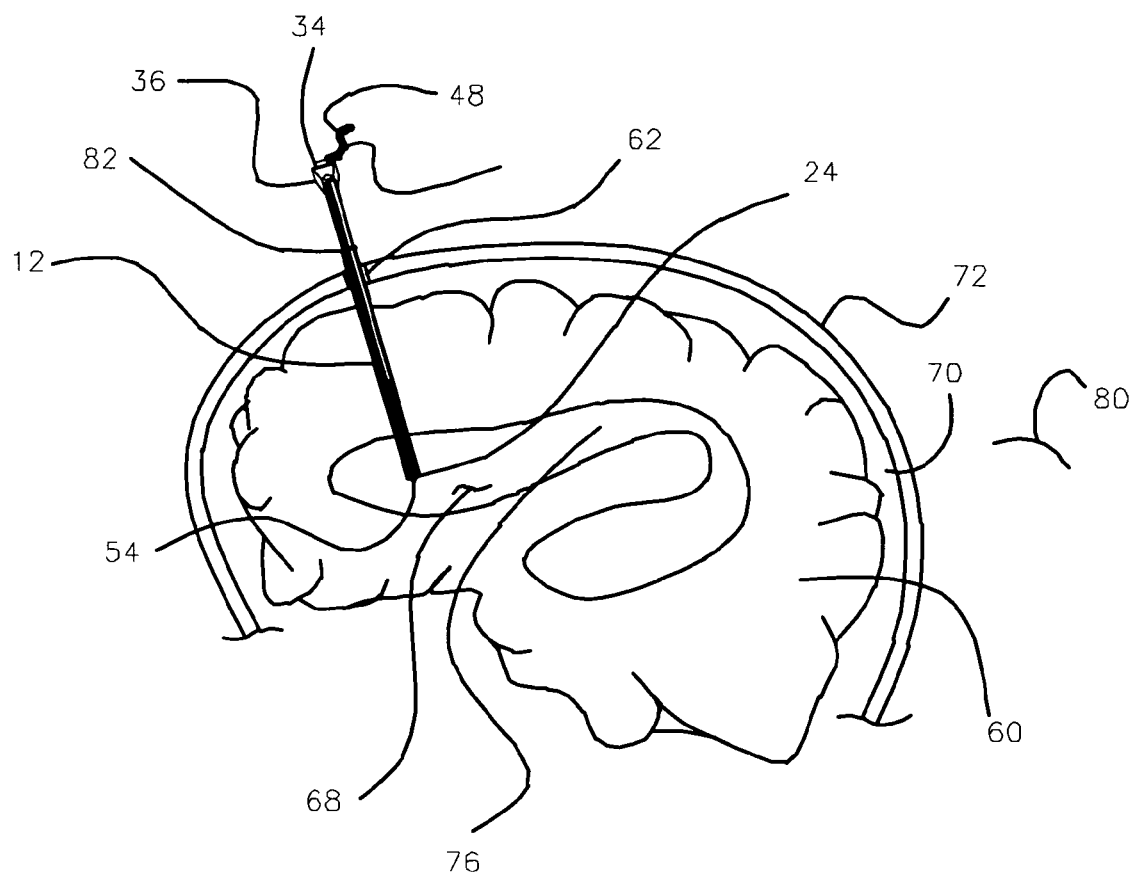
FIG. 2 illustrates the conduit as it may be inserted into a lateral ventricle of a brain.

As illustrated in FIG. 2, the stylet 14 is inserted into the conduit 12 and a distal end 24 of the conduit 12 penetrates brain tissue 60 through a surgical opening 62. As shown in FIG. 2, the distal end 24 resides within a lateral ventricle 68 while the side ports 16, 18, 20 on the conduit may be open to the subarachnoid/subdural space(s) 70. The conduit 12 may have variations in placement in other brain spaces, or cavities, such as, for example the subarachnoid space 70, as hereinafter described. The conduit 12 may have variations in design such that no side holes are provided for openings to the subarachnoid/subdural space(s) 70. The conduit 12 may have its distal end 24 in the lateral ventricle or its distal end 24 in the subarachnoid/subdural space(s) 70.

The stylet 14 with the fiber optics 52 increases the tensile strength of the conduit 12 to facilitate insertion of the conduit 12 into the brain 60 through the surgical opening 62 in a skull 72.

The stylet 14 enables visualization of proper placement of the conduit and when the conduit 12 is verified to be properly aligned within the lateral ventricle 68 and/or subarachnoid/subdural space(s) 70 the stylet 14 is withdrawn from the conduit 12 and the conduit 12 is secured to the skull 72 using surgical techniques.

At this time, back flow of cerebral spinal fluid (CSF) 76 residing in the brain's ventricular/subarachnoid/subdural areas 68, 70 should occur after removal of the stylet 14 and this further insures that the conduit 12 is properly inserted into the lateral ventricle 68 of the brain with side ports 16, 18, 20 open to the subarachnoid/subdural space(s) 70 or the distal end 24 of conduit 12 resides in the subarachnoid/subdural space(s) 70 only.

Referring again to FIG. 1, a one-way valve 86 or other device, disposed at the conduit proximal end 26, prevents continual drainage of CSF 76 from the brain 60. In cases of brain herniation/movement, the conduit 12 simply bends in the direction of herniation/movement, thus eliminating or minimizing any cerebral CNS injury.

Figure 3:
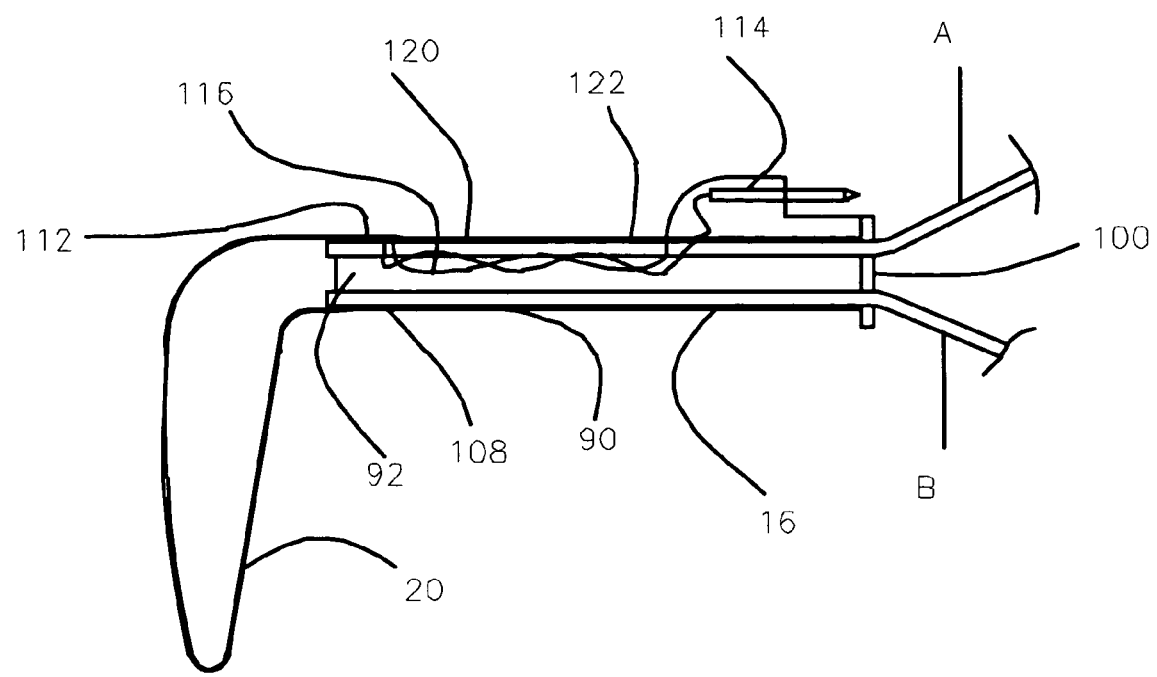
FIG. 3 is an expanded cross sectional view of a distal end of the elongated device, shown in FIG. 1, also showing a thermister and a thermister connector.

With reference to FIG. 3, there is shown the device 16 with the balloon 20 inflated and connected to a hollow tube 90 with a lumen 92 therethrough. Tube catheters A, B are attached inside the tube 90 for circulating fluid in the balloon for inflation and cooling purposes. The irrigation catheter A includes a connector 96 (FIG. 1) and the aspiration catheter B includes aspiration connector 98 (FIG. 1).

As most clearly shown in FIG. 3, a seal 100 located at the proximal end of probe 16 and a seal located at a distal end 108 of probe 16 may be provided to prevent escape of fluid to the environment. Alternatively, a needle septum 104 may be provided to inject additional pharmacological agents or artificial spinal fluids into the CSF by way of a port 106 at a distal end 108 of the device 16, see FIG. 1.

A thermister 112 may be disposed at the distal end 108 of the device 16 for providing direct temperature measurement of the CSF in the lateral ventricle 68, the thermister 112 being coupled to a connector 114 by way of wires, not shown. Alternatively, a bore, or tunnel, 120 (See FIG. 3) in a tube wall 122 may enable placement of the thermister 112 anywhere along the device 16 with wires running therethrough (not shown in FIG. 3).

Figure 4:
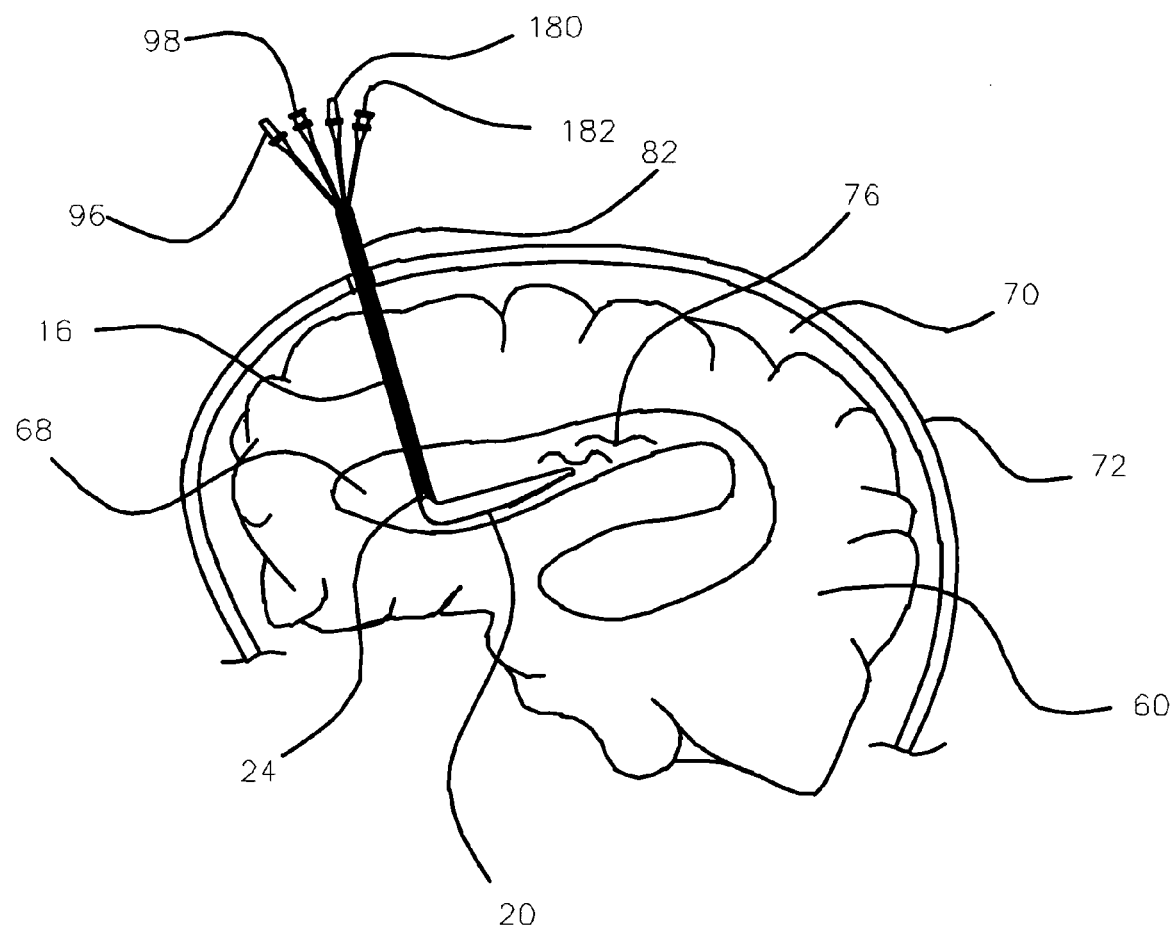
FIG. 4 illustrates the elongated device as inserted through the conduit having the balloon inflated.
Figure 5:
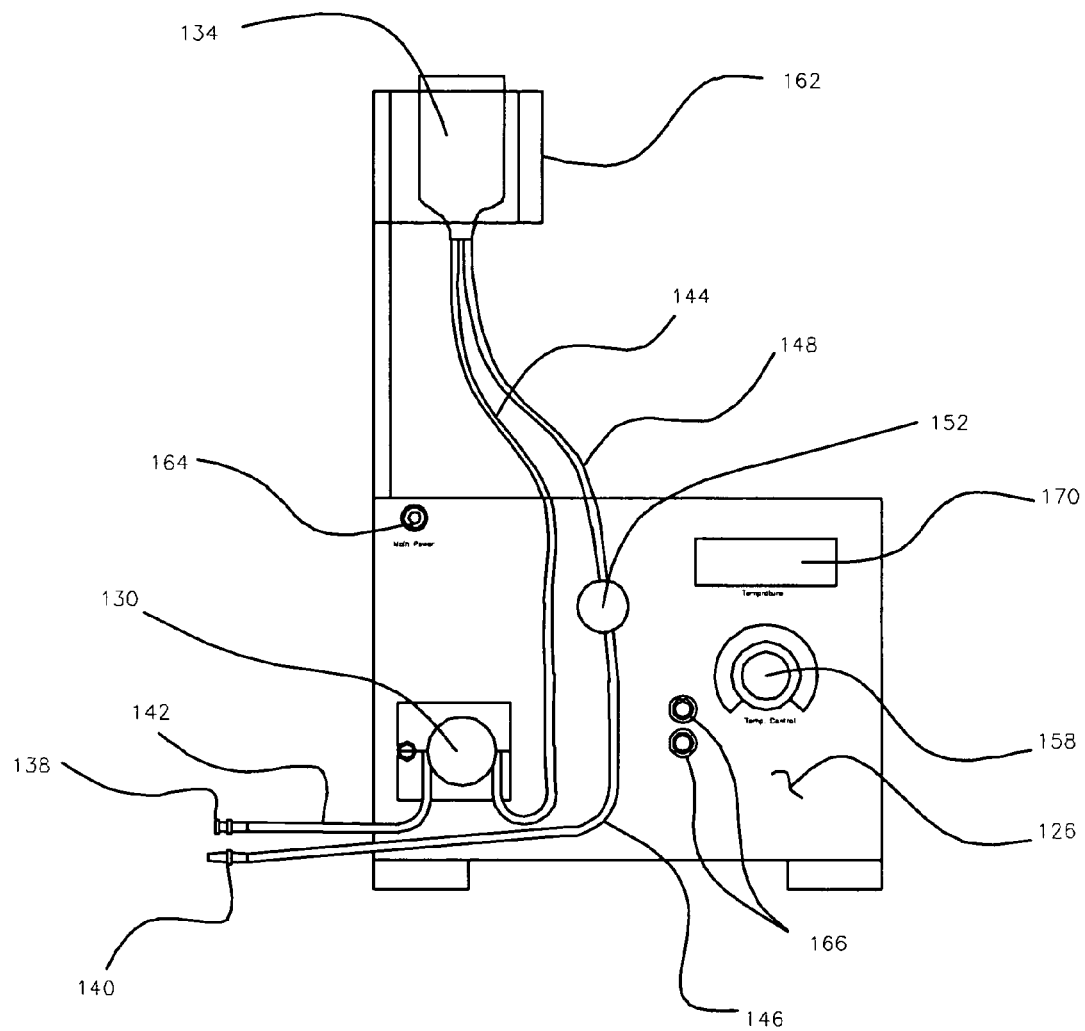
FIG. 5 diagrams apparatus for controlling fluid flow to and from the device and balloon.

FIG. 4 illustrates the placement of the device, or probe, 16 and the balloon 20 inflated and disposed for cooling the lateral ventricle 68 of the brain 60. With reference to FIG. 5, a control system includes a pump 130 interconnected between an irrigation catheter A and an aspiration catheter B (See FIG. 1) and a bottle 134 of suitable fluid through connectors 138, 140 and lines 142, 144, 146, 148. A pinch valve 152 or other device further controls fluid flow.

Pressure within the balloon 20 is adjusted by changing the height of the bottle 134 on a support pole 156 and a temperature control 158 controls a temperature regulator 162 surrounding the bottle 134.

The control system 126, shown in FIG. 5, in diagram form, includes conventional controls 166 and a display screen 170, all of which may be assembled with conventional components.

Figure 6:
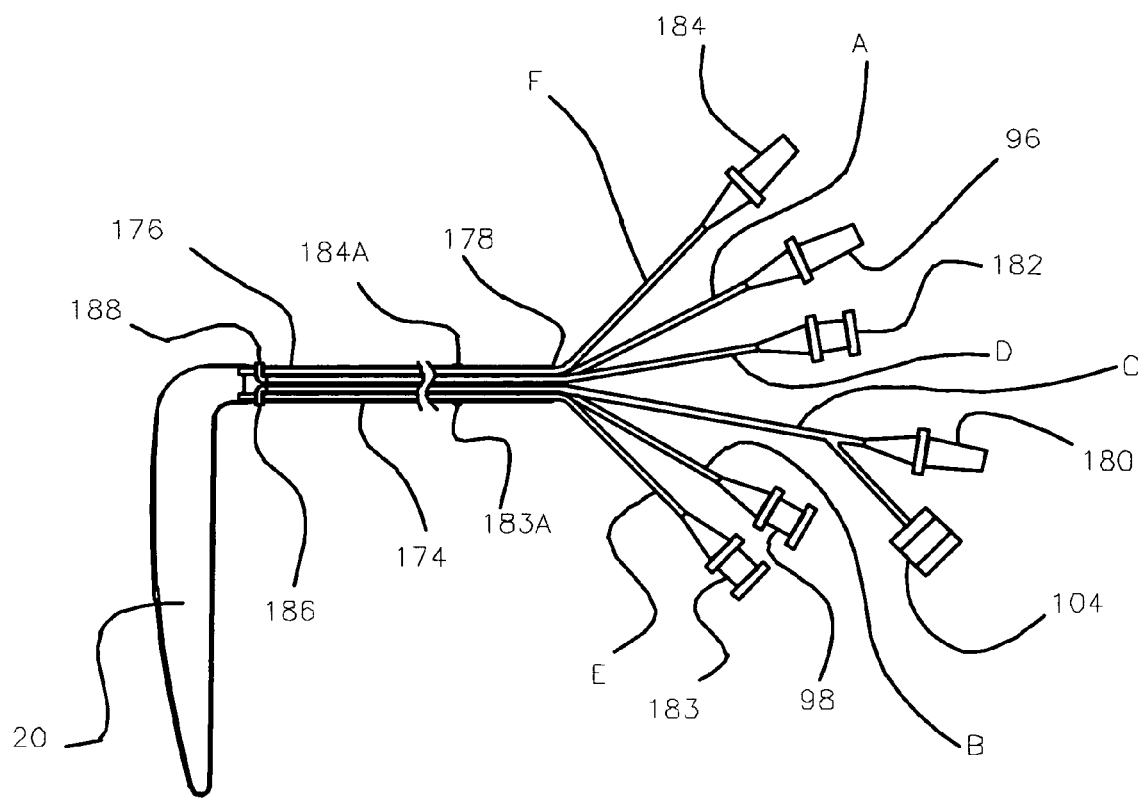
FIG. 6 is an alternative embodiment of the cooling device illustrating the use of six catheters, two for circulating fluid within the balloon and four for circulating CSF within the brain cavities.

It should be further appreciated that the device 16 may be utilized without the balloon 20. In this embodiment the CSF is circulated through the catheters A, B. Further, both direct circulation of CSF for cooling and indirect cooling of the lateral ventricle 68 or subarachnoid/subdural space(s) 70 may be performed with an alternative embodiment or cooling probe device 174, as shown in FIG. 6.

Similar to the device 16, the device 174 includes a hollow tube 176 with the irrigation catheter A and aspiration catheter B disposed inside the tube 176 and exiting a proximal end 178 of the tube 176 and fitted with connectors 96, 104, as hereinabove described. The catheters A and B operate to inflate the balloon and circulate the fluid therein for cooling of the brain 60, as hereinabove described.

An additional irrigation catheter C and aspiration catheter D are provided and also disposed within the tube 176 and communicate with connectors 180, 182 respectively. A needle septum 104, as shown in FIG. 1, (for administration of pharmacological agents, fluids, or other compounds)may also be provided as hereinabove described.

The device (174) may alternatively include another irrigation catheter E and another aspiration catheter F disposed within the tube 176 and communicate with connectors 183, 184 respectively. The distal end of irrigation catheter E exits through a side port 183A in device 174 to reside in the subarachnoid/subdural space(s) 70. Similarly, the distal end of aspiration catheter F also exits through a side port 184A in device 174 which would reside in the subarachnoid/subdural space(s) 70.

Figure 7:
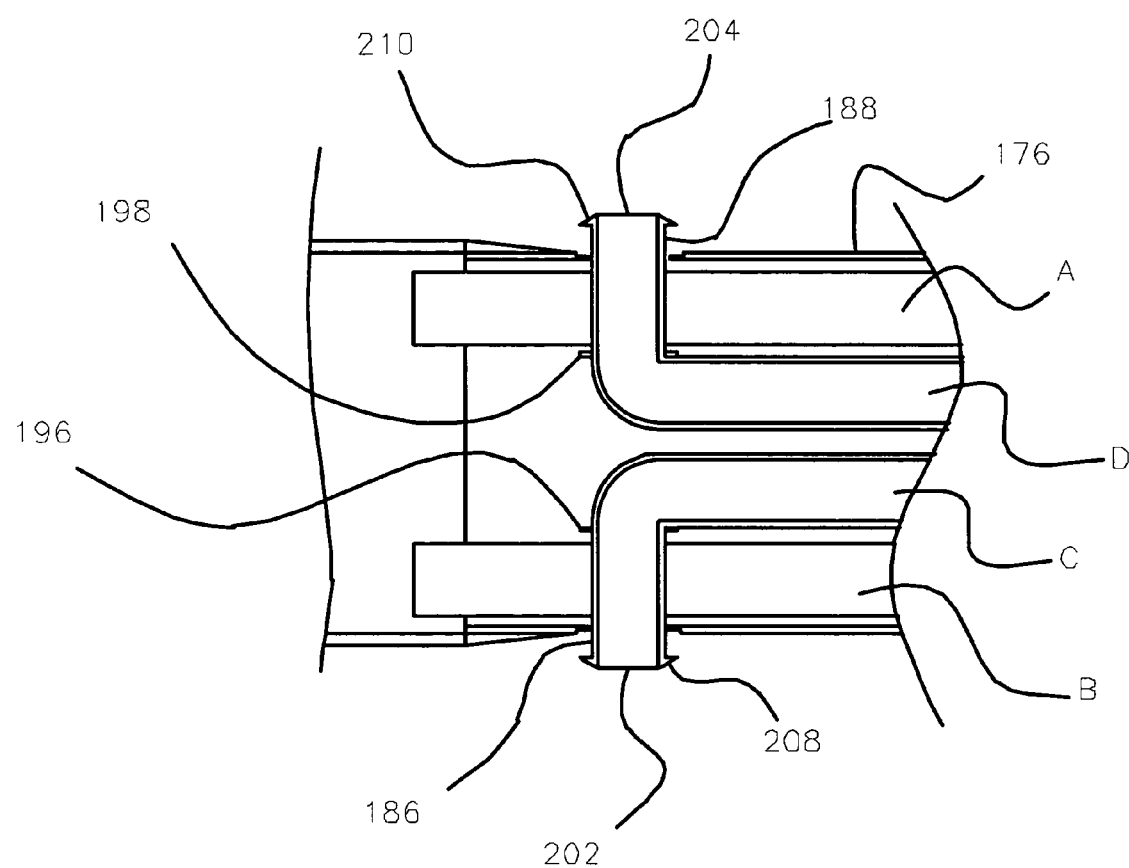
FIG. 7 is an enlarged cross sectional view showing the distal end of the device, shown in FIG. 6, detailing the ends of the four catheters.
Figure 8:
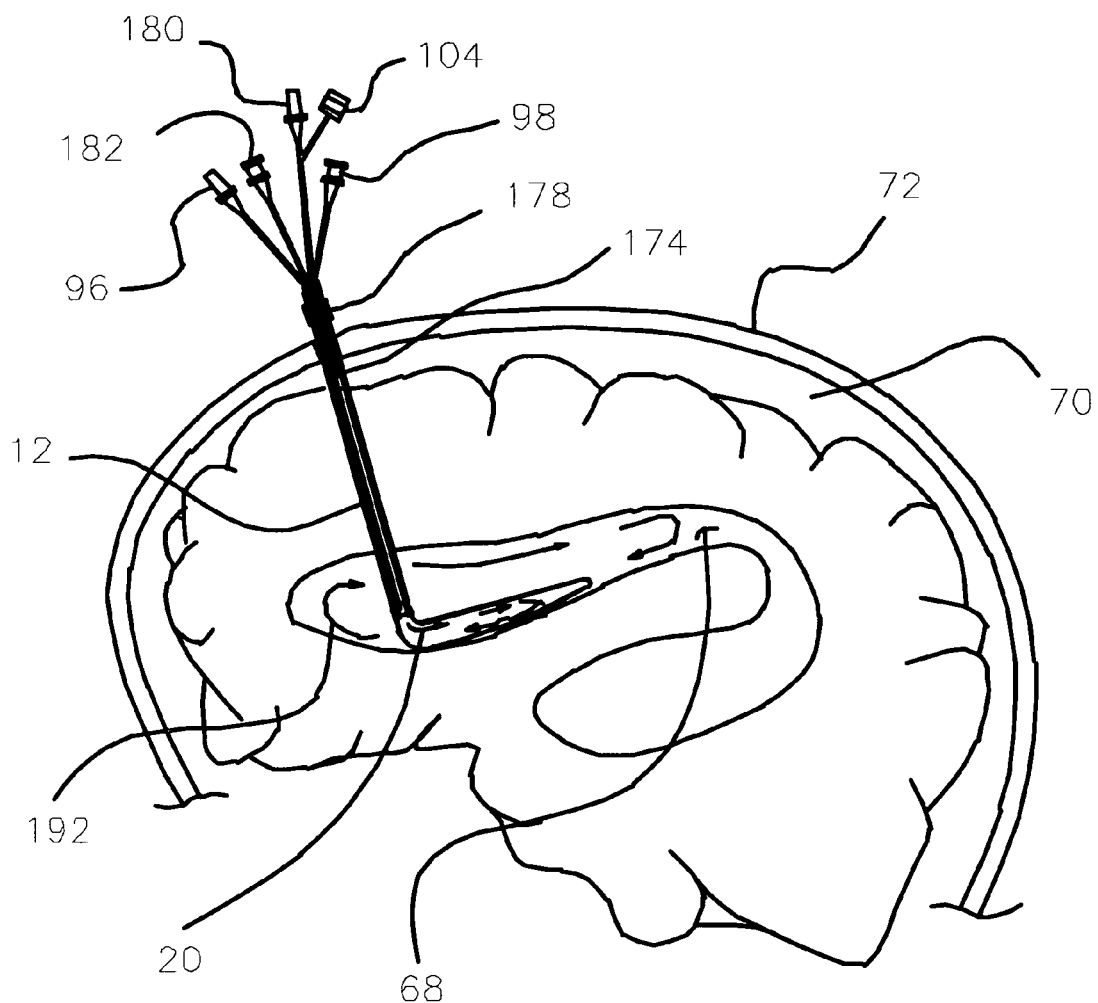
FIG. 8 is a diagram showing the four-catheter device inserted into the conduit and circulation patterns of fluid within the inflated balloon and within the lateral ventricle of the brain.

As more clearly shown in the enlarged partial cross section of FIG. 7, the catheters C and D include exit ports 186, 188 extending through the tube 176 at approximately 180° relationship with one another. This facilitates the circulation of CSF within the lateral ventricle 68 as indicated by the arrows 192 in FIG. 8. The catheters C and D include stoppers 196, 198 to prevent distal ends 202, 204 advancing too far outside the probe tube 176. Additional stoppers 208, 210 on the distal ends 202, 204, the catheters at C and D prevent the distal ends 202, 204 from entering the tube 176 and also providing a flush fit with the tube 176 in order to facilitate the insertion of the probe 174 into the conduit 12. Similarly, the distal ends of catheter's E and F will exit through side ports 183A, 184A of device 174 to reside within the subarachnoid/subdural space(s) 70.

Operation of the cooling probe device 174 is managed by a control system 212 (See FIG. 9) having elements identical to or similar to that described in connection with the system 126 with common reference characters representing identical or substantially similar components.

Figure 9:
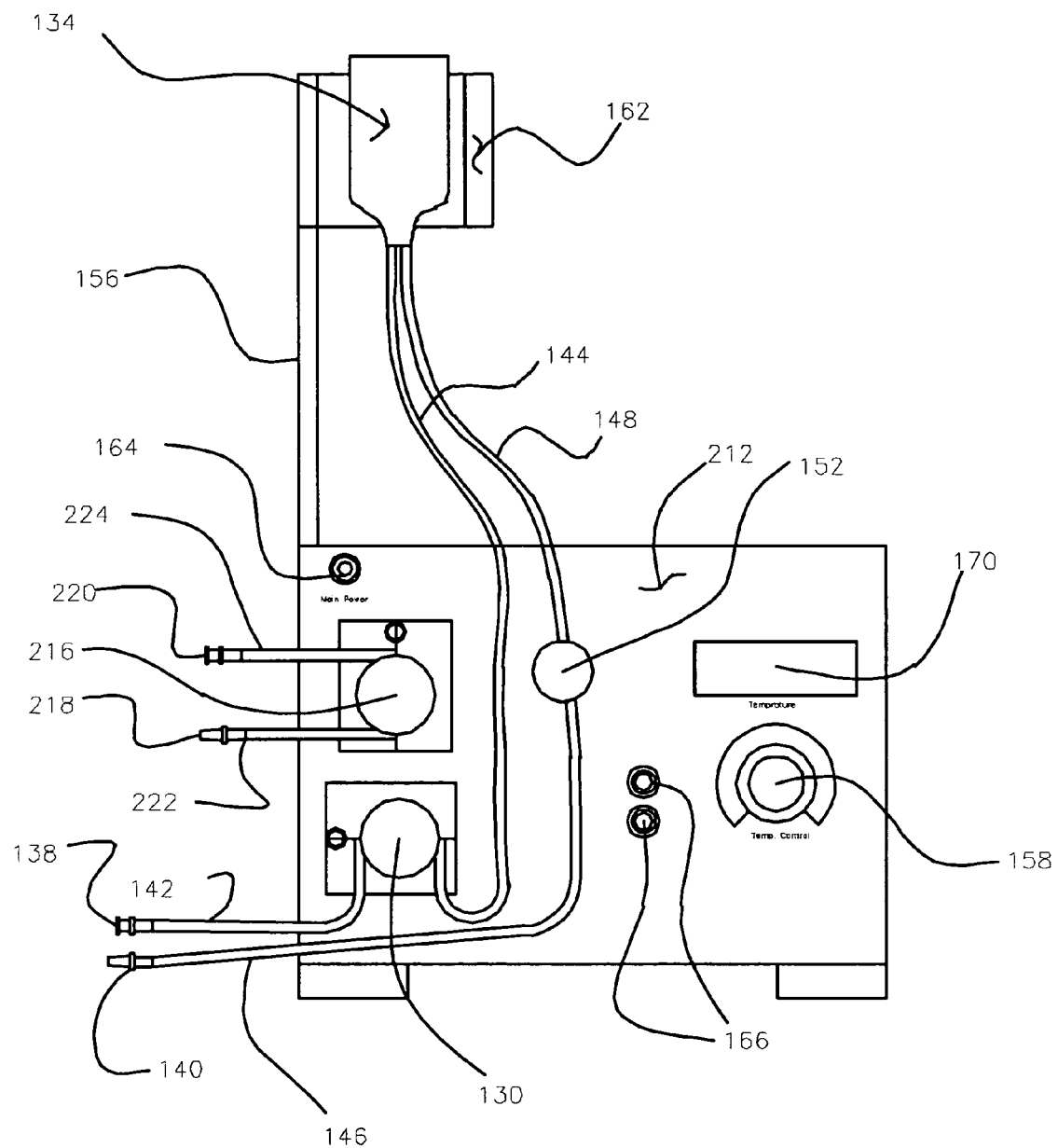
FIG. 9 is a diagram of a control system for regulating fluid to the four catheter elongated device.

This system 212 further includes pumps and/or temperature control devices 216 for circulating CSF through the catheters C and D as well as E and F by way of an irrigation fitting 218 and an aspiration fitting 220 and an irrigation aligned 222 and aspiration line 224 respectively, only one being shown in FIG. 9 for clarity. With catheters C, D, E, and F in place, simultaneous cooling and/or heating and/or circulation of the subarachnoid/subdural 70 and lateral ventricular space(s) 68 can take place. Furthermore, circulation within the lateral ventricle and the subarachnoid space(s) 70 can be controlled independently.

Variations of the above cooling and/or heating and/or circulating schemes can occur. The distal end of catheter C may be exposed to the lateral ventricular space while the distal end of catheter D may be open to the subarachnoid/subdural space(s) 70 through the side ports 183A, 184A on device 174, or vice-versa. Thus, cerebro-spinal fluid (CSF) will be aspirated from catheter D and irrigated through catheter C creating circulation between the subarachnoid/subdural space(s) 70 and the ventricular spaces, or vice-versa.

Alternatively, the distal ends of catheter C and D may solely be exposed to the subarachnoid/subdural space(s) 70 through the side ports 183A, 184A of device 174. Thus, circulation will be localized in the subarachnoid/subdural spaces 70 in this fashion.

Another embodiment of the circulation scheme once again places the distal ends of catheters C and D into the lateral ventricle while the distal ends of catheters E and F are open to the subarachnoid/subdural space(s) 70. However, in this case one pump controls circulation by aspirating fluid from catheters D and F while irrigating fluid through catheters C and E. Once again simultaneous circulation is achieved within the lateral ventricular and subarachnoid/subdural space(s) 70, but only one pump is used in this manner.

Figure 10:
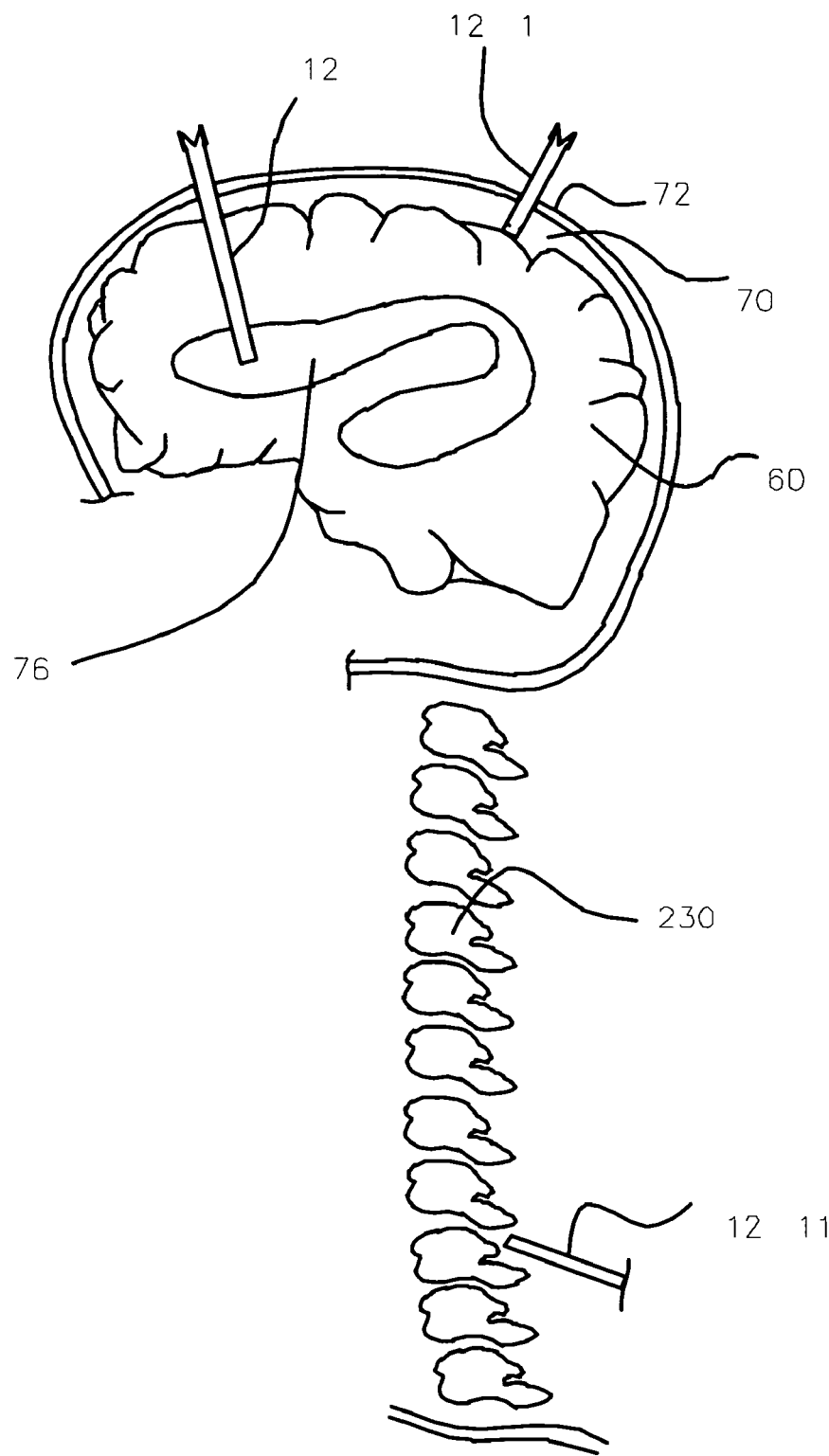
FIG. 10 is a diagram showing the installation of three devices, one in the lateral ventricle of the brain, another in a subarachnoid and the brain and yet another spinal insert for circulation of CSF.

With reference to FIG. 10 there is shown alternate placement of the conduit 12, 12', 12", which may be used simultaneously with separate devices 16, 174 for enabling circulation of CSF throughout the brain 60 and spinal cord 230.

In addition, the conduits 12, 12', 12" provide access to the brain and spinal cord for other instrumentation to be utilized, such as, for example, pressure measurement device disposed adjacent to the thermister 112 or otherwise inserted in one of the catheters A, B, C or, D. Ultrasonic transducers, not shown, may also be introduced to the brain or spinal cord by way of the conduits 12, 12', 12".

Figure 11:
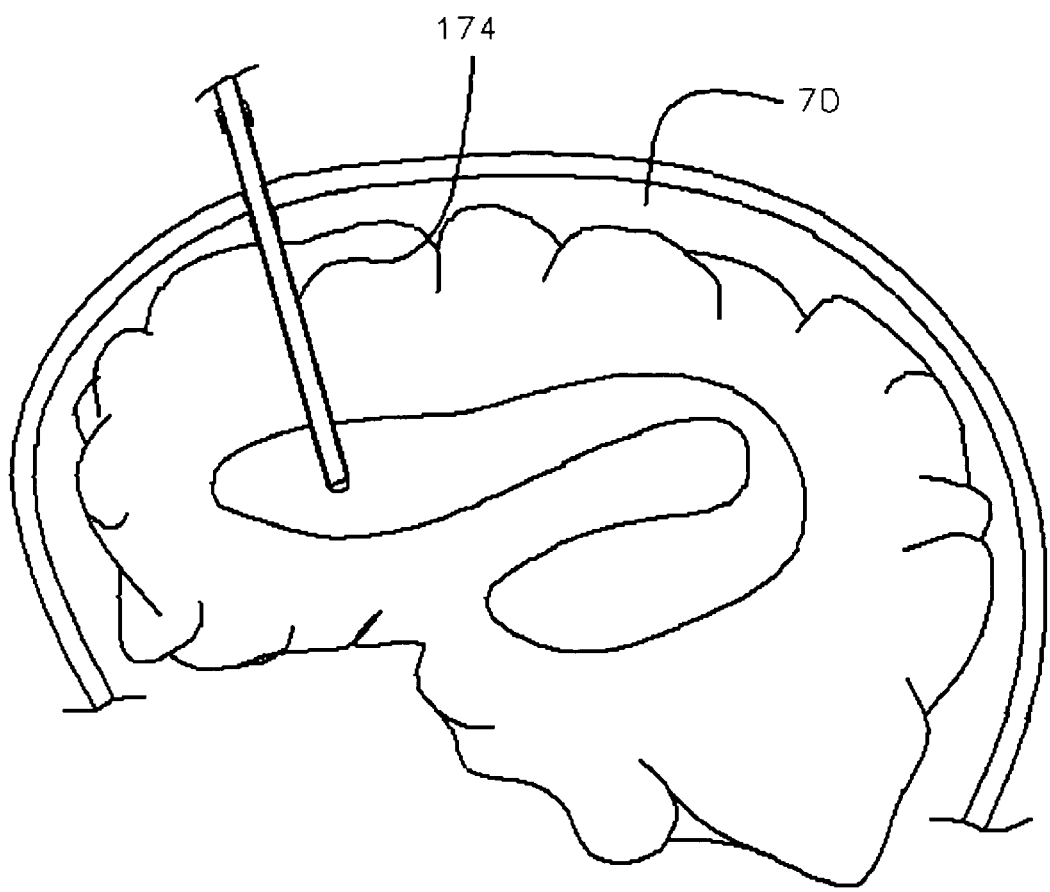
FIG. 11 is a diagram showing another configuration of the present invention to ensure rapid cooling of the neurons in the cortex and paraventricular areas simultaneously. There is a single probe with conduits in the lateral ventricles for temperature control as well as conduits in the subarachnoid space and or subdural space for temperature control simultaneously.

FIG. 11 shows a variation of device 174 without the balloon 20. In this scheme, the distal end of irrigation catheter A and aspiration catheter B is exposed to the cerebrospinal fluid (CSF) in the lateral ventricle. Moreover, the distal end of irrigation catheter C and aspiration catheter D is exposed to the subarachnoid/subdural space(s). In this fashion the cooling and/or heating and/or circulating of the CSF can simultaneous occur in the cerebral cortex as well as the areas adjacent to the periventricular nuclei. Circulation between catheters A, B, C, and D can occur with the use of one or more pumps. Thus catheters A and B (connected serially by tubing) and catheters C and D (connected serially by tubing) may be connected to multiple pumps to independently control aspiration and irrigation through their opening.

Figure 12:
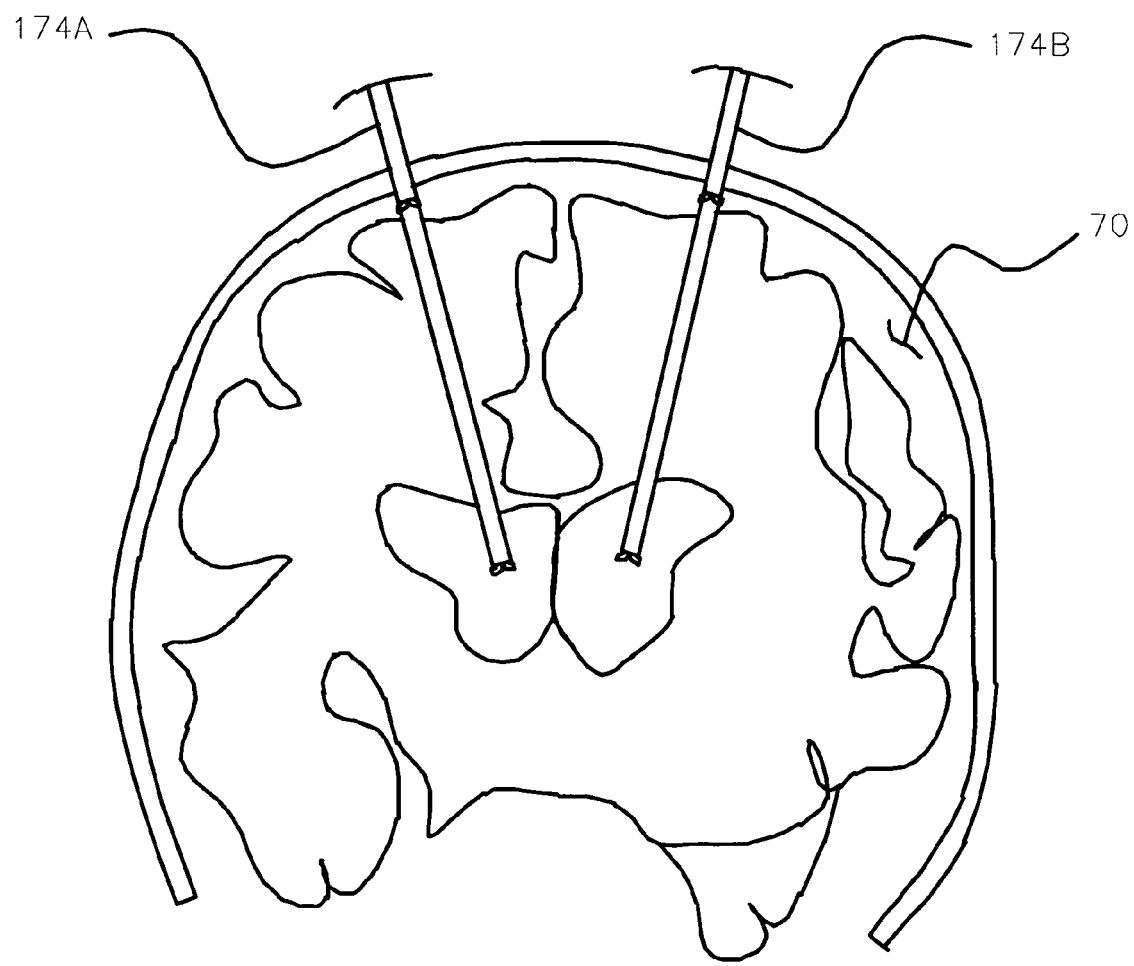
FIG. 12 is a diagram showing yet another configuration of the present invention similar to that shown in FIG. 11 but with two probes in the lateral ventricles.

Multiple devices can be inserted into the central nervous system (CNS). Some variations of this method are depicted in FIG. 12. Simultaneous cooling and/or heating and/or circulation can be achieved within both cerebral hemispheres of the central nervous system in the lateral ventricular and subarachnoid/subdural space(s). Alternatively, cooling and/or heating and/or circulation can be isolated to the subarachnoid/subdural space(s) and/or lateral ventricular space of one or both hemispheres.

Although there has been hereinabove described a specific medical device and method for temperature control and treatment of the brain and spinal cord in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element, which is not specifically disclosed herein. Accordingly, any and all modifications, variations or equivalent arrangements which may occur to those skilled in the art, should be considered to be within the scope of the present invention as defined in the appended claims.

What is claimed is:

1. A method of preventing neurological damage, said method comprising the steps of:
   inserting an elongated device into a lateral ventricle;
   inflating a balloon disposed at an end of the device with a fluid; and
   controlling an internal temperature of the brain by circulating the fluid within said balloon.

2. The method according to claim 1 wherein circulating the fluid within said balloon comprises providing irrigation fluid into said balloon through a catheter disposed in said elongated device and aspirating fluid from said balloon through an aspiration catheter.

3. The method according to claim 1 wherein the step of controlling the internal temperature of the brain includes cooling of the brain directly in order to decrease systemic side effects of hypothermia including cardiac arrhythmias, cerebrovascular accidents, and bleeding diathesis.

4. The method according to claim 1 wherein the step of controlling the internal temperature of the brain includes cooling of the brain to reduce swelling of brain tissue.

5. The method according to claim 1 wherein the step of controlling the internal temperature of the brain includes pretreatment and post-treatment of the brain in neurosurgical procedures.

6. The method according to claim 1 further comprising the step of administering fluid and medication into the brain via said elongated device.

7. The method according to claim 1 further comprises the step of inserting a conduit into the brain with a stylet therein; positioning the conduit through the use of a fiber optic camera with a lens at a distal end of said conduit; removing said stylet and thereafter inserting said elongated device.

8. A method of preventing neurological damage, said method comprising the steps of:
   inserting an elongated device with a deployable expendable balloon shaped device that allows for fluid exchange into a lateral ventricle; and
   controlling an internal temperature of the brain by circulating of cerebrospinal fluid into and out of the lateral ventricle.

9. A method of preventing neurological damage, said method comprising:
   inserting an elongated device into a lateral ventricle;
   controlling an internal temperature of the brain by circulating of cerebrospinal fluid into and out of the lateral ventricle; and
   inflating a balloon disposed at an end of the device with a fluid and further controlling the internal temperature of the brain by circulating the fluid within said balloon.

10. The method according to claim 9 wherein circulating the fluid within said balloon comprises providing irrigation fluid into said balloon through a catheter disposed in said elongated device and aspirating fluid from said balloon through an aspiration catheter.

11. The method according to claim 10 wherein circulating of cerebrospinal fluid is performed through inlet and outlet catheter disposed in said elongated device and ports communicating with the lateral ventricle.

12. The method according to claim 1 wherein the step of controlling the internal temperature of the brain includes cooling of the brain in the lateral ventricle and the subarachnoid and/or subdural space simultaneously using principles of convection and conduction cooling.

13. The method according to claim 11 wherein the step of controlling the internal temperature of the brain includes cooling of the brain to reduce swelling of brain tissue.

14. The method according to claim 11 wherein the step of controlling the internal temperature of the brain includes pretreatment and post-treatment of the brain in neurosurgical procedures.

15. The method according to claim 11 further comprising the step of administering fluid and medication into the brain via said elongated device.

16. The method according to claim 11 further comprising the step of inserting a conduit into the brain with a stylet therein; positioning the conduit through the use of a fiber optic camera with a lens at a distal end of said conduit; removing said stylet and thereafter inserting said elongated device.

17. The method according to claim 1 further comprising the step of introducing a needle into a subarachnoid space of the spinal cord and circulating cerebrospinal fluid between the elongated device and said spinal tap to control brain temperature and spinal cord temperature.

18. Apparatus for preventing neurological damage, said apparatus comprising:
   an elongate device for insertion into a lateral ventricle or other space of a brain through a surgical opening, the device having a proximal and a distal end;
   a balloon disposed at the distal end;
   a catheter disposed in the device for introducing a fluid into said balloon;
   an aspiration catheter disposed in the device for aspirating the fluid from said balloon;
   a pump interconnecting said catheter and aspiration catheter for circulating fluid within said balloon for controlling an internal temperature of the brain;
   a conduit for insertion into the brain and sized for receiving the device therein; and a stylet, said stylet having a fiber optic camera with a lens at a distal end therein for positioning said conduit within the brain.

19. The apparatus according to claim 18 further comprising at least one temperature sensor disposed in the device for measuring temperature along the device.

20. The apparatus according to claim 19 further comprising means for heating and cooling said fluid.

21. The apparatus according to claim 20 further comprising a third catheter introducing medication into said brain.

22. The apparatus according to claim 21 further comprising fourth and fifth catheters disposed in the device for aspirating cerebrospinal fluid from the brain and introducing cerebrospinal fluid into the brain.

23. The apparatus according to claim 22 further comprising a second device for insertion into another surgical opening into the brain and spinal cord for circulation of cerebrospinal fluid between said brain and said spinal cord and a temperature controller disposed exterior to said brain and spinal cord.

* * * * *